United States Patent [19]

Weis et al.

[11] Patent Number: 4,897,484

[45] Date of Patent: Jan. 30, 1990

[54] PROCESS FOR THE PREPARATION OF SUBSTITUTED PYRIDINES

[75] Inventors: Claus D. Weis, Pfeffingen; Peter Sutter, Muttenz, both of Switzerland

[73] Assignee: Ciba-Geigy Corporation, Ardsley, N.Y.

[21] Appl. No.: 130,486

[22] Filed: Dec. 9, 1987

[30] Foreign Application Priority Data

Dec. 19, 1986 [CH] Switzerland ............... 5096/86

[51] Int. Cl.⁴ ............... C07D 213/133; C07D 213/08; C07D 211/02
[52] U.S. Cl. ................... 546/252; 546/250; 546/266; 546/284; 546/286; 546/219
[58] Field of Search ............... 546/252, 250, 345, 219

[56] References Cited

U.S. PATENT DOCUMENTS 3,849,422 11/1974 Weis ................... 546/252
4,414,156 11/1983 Scherrer et al. ............ 260/352
4,604,243 8/1986 Davidson ............... 558/388

OTHER PUBLICATIONS

Journal of Heterocyclic Chemistry, 24: #4 (1987) pp. 1093–1102.
Hel. Chem. Acta 59, pp. 190–220.

Primary Examiner—Alan L. Rotman
Attorney, Agent, or Firm—Kevin T. Mansfield; Edward McC. Roberts

[57] ABSTRACT

A process is described for the preparation of compounds of the formula

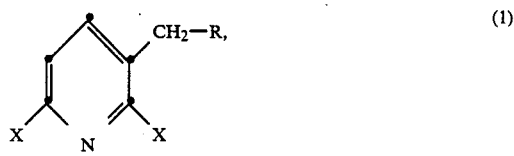

in which R and X are as defined in claim 1.

The compounds of the formula (1) are valuable intermediates in the synthesis of triarylmethane dyes and triarylmethanelactones.

14 Claims, No Drawings

PROCESS FOR THE PREPARATION OF SUBSTITUTED PYRIDINES

The invention relates to a process for the preparation of 2,6-dihalogeno-3-arylmethylpyridines, which are valuable intermediates in the synthesis of triarylmethane dyestuffs and triarylmethanelactones.

A process for the prepartion of 2,6-dichloro-3-arylmethylpyridines, in which the aryl compound is reacted with 2,6-dichloro-3-chloromethylpyridine in a Friedel-Crafts alkylation reaction is already known, for example from U. Horn, F. Mutterer and C. D. Weis, Helv. Chim. Acta 59, 190 et seq (19676). Hidden in this process, however, is the disadvantage that, in the case of substituted aryl compounds, a single-substance product is generally not obtained, but only a mixture of compounds, different position isomers, which must first be separated laboriously. In addition, the process described only makes it possible to prepare 2,6-dihalogenopyridines containing a carbocyclic arylmethyl radical, but not those containing a heterocyclic arylmethyl radical in the 3-position.

A universally applicable process for the preparation of 2,6-dihalogeno-3-arylmethylpyridines has now been found, which makes it possible to introduce an incalculable number of carbocyclic and heterocyclic arylmethyl substituents into the 3-position of 2,6-dihalogenopyridines.

The invention therefore relates to a process for the preparation of compounds of the formula

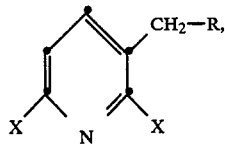

(1)

in which X is halogen and R is a carbocyclic or heterocyclic aromatic radical, which comprises the following process stages:

(a) diazotizing a compound of the formula

  R—NH$_2$    (2)

in the presence of a polar organic solvent, an acid and a diazotization reagent, and reacting the diazotized compound with 2-methyleneglutaronitrile in the presence of a catalyst, (b) cyclizing the compound of the formula

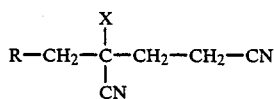

(3)

obtained in accordance with (a) in an acid medium to give the piperidine-2,6-dione compound of the formula

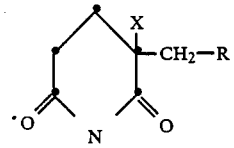

(4)

and (c) aromatizing the piperidine-2,6-dione compound of the formula (4) in the presence of a dehydrating solvent, R and X each being as defined in formula (1).

In the compounds of the formula (1) X is halogen, for example bromine and especially chlorine.

R in formula (1) is a carbocyclic or heterocyclic aromatic radical; this is preferably the radical of a carbocyclic $C_6$–$C_{18}$ aromatic compound or the radical of a monocyclic or bicyclic heteroaromatic compound containing one or more N, S and/or O atoms.

The radical R can be unsubstituted or monosubstituted or polysubstituted by identical or different radicals. Examples of suitable substituents are $C_1$–$C_4$-alkyl, such as methyl, ethyl, n-propyl, isopropyl or n-, sec.- or tert.-butyl, $C_1$–$C_4$-alkoxy, such as methoxy, ethoxy, n-propoxy, isopropoxy or n-, sec.- or tert.-butoxy, halogen, such as fluorine, chlorine or bromine, nitro, cyano, trifluoromethyl or $C_1$–$C_4$alkoxycarbonyl, such as methoxycarbonyl, ethoxycarbonyl, n-propoxycarbonyl, isopropoxycarbonyl or n-, sec. or tert.-butoxycarbonyl.

R is preferably a phenyl, naphthyl, pyridyl or thienyl radical which is unsubstituted or substituted, for example, by the radicals mentioned above.

One group of useful compounds of the formula (1) which can be prepared by the process according to the invention embraces compounds in which R is a carbocyclic aromatic radical; in this case R is preferably a naphthyl and, in particular, a phenyl radical which is unsubstituted or substituted as described above. The process is particularly suitable for the preparation of compounds of the formula (1) in which R is a phenyl radical which is unsubstituted or substituted by methyl, ethyl, methoxy, ethoxy, chlorine, fluorine, nitro, cyano, methoxycarbonyl and/or ethoxycarbonyl.

Another group of useful compounds of the formula (1) which can be obtained by means of the process according to the invention embraces compounds in which R is a heterocyclic aromatic radical; in this case R is preferably the radical of a monocyclic or bicyclic heterocyclic structure containing 1 or more N and/or S atoms. Examples of suitable heterocyclic radicals R are the radical or pyridine or thiophene, it being possible for these radicals to be substituted by the substituents mentioned above.

As a heterocyclic radical, R is particularly preferably a pyridin-3-yl or thien-3-yl radical which is unsubstituted or substituted by methyl, chlorine, methoxycarbonyl or ethoxycarbonyl.

In the amines of the formula (2) which are employed in the process in accordance with the invention, the abovementioned meanings and preferences apply to R. Accordingly, R—NH$_2$ as a carbocyclic aromatic amine is preferably an aniline or naphthylamine which is unsubstituted or substituted as described above. Examples of preferred heterocyclic aromatic amines of the formula (2) are unsubstituted or substituted 3-aminopyridine or 3-aminothiophene; particularly preferred heterocyclic amines of the formula (2) are 3-aminopyridine or 3-aminothiophene each of which is unsubstituted or substituted by methyl, chlorine, methoxycarbonyl or ethoxycarbonyl.

The polar organic solvent in process stage (a) is, for example, a dimethyl alkanephosphonate having 1 to 4 C atoms; examples of other suitable solvents are $C_1$–$C_4$ alkanols, for example methanol, ethanol, n-propanol, isopropanol, n-butanol or isobutanol, $C_1$–$C_4$ ketones, for example acetone, $C_4$–$C_{10}$ glycol ethers, such as diethylene glycol dimethyl ether or diethyl ether, formamides, such as formamide, n-methylformamide, N,N-dimethylformamide or N,N-diethylformamide, or cyclic sulfones, for example sulfolane.

It is preferable to use dimethyl $C_1$–$C_2$-alkanephosphonates, methanol, acetone, diethylene glycol dimethyl ether, diethylene glycol diethyl ether, N,N-dimethylformamide or sulfolane as the solvent in reaction stage (a); the particularly preferred solvent is dimethyl methanephosphonate.

The polar organic solvent is employed, for example, in a weight ratio of 2:1 to 10:1, relative to the amine of the formula (2).

The diazotization agents used are esters of nitrous acid, particularly those of primary or secondary alcohols having 1 to 10 carbon atoms. Examples of such esters are the liquid nitrites of isopropyl, butyl, pentyl, isopentyl, heptyl and decyl alcohols, which have a boiling point above 50° C.; it is advantageous to use the esters of alcohols having 1 to 5 carbon atoms, for example methyl, ethyl, propyl, isopropyl, isobutyl or isopentyl nitrite, which are gaseous or liquid. The esters can be added to the reaction mixture as such or dissolved in a solvent, for example in the same solvent in which the reaction takes place; the lowboiling esters can also be introduced in the gaseous state. It is preferable to use isopentyl or methylnitrite.

The diazotization agent is advantageously employed in approximately stoichiometric amounts, relative to the amine of the formula (2).

The diazotization is carried out, as is generally customary, in the presence of an acid; examples of suitable acids are hydrobromic acid and, in particular, hydrochloric acid.

In general, the acid is present in at least equimolar amounts, preferably in an excess of up to 5 times molar, relative to the amine of the formula (2).

The diazotization, and also the reaction of the diazotized compound of the formula (2) with 2-methyleneglutaronitrile are carried out, for example, at a temperature from 20° to 100° C., preferably 35° to 75° C.

It is particularly preferably to carry out the diazotization and the reaction of the diazotized compound with 2-methyleneglutaronitrile simultaneously, since the diazotized compound is then always present only in small amaounts.

The 2-methyleneglutaronitrile is advantageously employed in a molar ratio of 1:1 to 5:1, preferably 1:1 to 2:1, relative to the amine of the formula (2).

Examples of suitable catalysts for the reaction of the diazotized amines of the formula (2) with 2-methyleneglutaronitrile are metallic iron or copper powder, iron or copper salts or mixtures consisting of iron powder and an iron salt or of copper powder and a copper salt; the metal salts are preferably the corresponding chlorides. If a mixture of metal powder and a metal salt is used, it is preferable to employ these two in a 1:1 ratio.

It is preferable to use catalytic amounts of copper powder, copper-(I) chloride or copper-(II) chloride; the use of copper-(I) chloride is particularly preferable.

The catalyst is employed in amounts of, for example, 0.1 to 5% by weight, preferably 0.5 to 2% by weight, relative to the amine of the formula (2).

A particularly preferred embodiment of process stage (a) of the present process relates to the diazotization of an amine of the formula (2) in the presence of an ester of nitrous acid having 1 to 5 C atoms, hydrochloric acid and dimethyl methanephosphonate, and the simultaneous reaction of the diazotized compound with 1 to 5 mol of 2-methyleneglutaronitrile per mol of amine of the formula (2), in the presence of 0.1 to 5.0% by weight, relative to the amine of the formula (2), of metallic copper powder, copper-(I) chloride or copper-(II) chloride at a temperature from 35° to 75° C.

The dinitriles of the formula (3) obtained in accordance with process stage (a) can be converted into the piperidine-2,6-dione compounds of the formula (4) in an acid medium at a temperature of, for example, 40° to 200° C., preferably 80° to 170° C. The acid medium consists, for example, of an inorganic or organic acid, for example hydrochloric acid, sulfuric acid, formic acid or acetic acid. Mixtures of different acids, especially mixtures of an inorganic and an organic acid, are also suitable.

A particularly preferred medium for the cyclization in accordance with process stage (b) is a mixture of acetic acid and sulfuric acid.

Examples of dehydrating solvents suitable for process stage (c) are phosphorus oxybromide and, particularly, phosphorus oxychloride; in each case an excess, relative to the compound of the formula (4), of the dehydrating solvent is employed.

The aromatization can be carried out without a catalyst or, preferably, in the presence of a catalyst; an example of a suitable catalyst is hexamethylphosphoric acid triamide (HMPT).

The catalyst is employed, for example, in an amount of 3 to 30% by weight, preferably 5 to 15% by weight, relative to the dehydrating agent.

The aromatization of the piperidine-2,6-dione compounds of the formula (4) is carried out, for example, at a temperature from 50° to 250° C., preferably at 100° to 200° C. and particularly preferably at 120° to 180° C.

The aromatization can be carried out in an open vessel under normal pressure or, preferably, in a closed vessel (autoclave) under a pressure which can, for example, be up to 10 bar, preferably up to 3 bar.

In a preferred embodiment of the process according to the invention the aromatization stage (c) is carried out in the presence of excess phosphorus oxybromide or phosphorus oxychloride and 5 to 15% by weight of HMPT, relative to the phosphorus oxyhalide, in a sealed vessel under pressure and at a temperature from 120° to 180° C.

The products from process stages (a), (b) and (c) can in each case be isolated and purified in a manner known per se, for example by filtration, crystallization, extraction, washing and/or distillation.

A particularly preferred embodiment of the process according to the invention for the preparation of compounds of the formula (1) indicated above is one wherein the process stages are as follows:

(a) diazotization of a compound of the formula (2) indicated above in the presence of an ester of nitrous acid having 1 to 5 C atoms, hydrochloric acid and dimethyl methanephosphonate, and simultaneous reaction of the diazotized compound with 1 to 5 mol of 2-methyleneglutaronitrile per mol of amine of the formula (2) in the presence of 0.1 to 5% by weight of copper powder, copper-(I) chloride or copper-(II) chloride, relative to the amine of the formula (2), at a temperature of 35° to 75° C., to give the compound of the formula (3) indicated above;

(b) cyclization of the compound of the formula (3) indicated above in a mixture of sulfuric acid and acetic acid at a temperature from 40° to 200° C. to give the piperidine-2,6-dione compound of the formula (4) indicated above, and (c) aromatization of the compound of the formula (4) indicated above in the presence of excess phosphorus oxychloride or oxybromide and 5–15% by weight of hexamethylphosphoric acid triamide, relative to the phosphorus oxyhalide, in a sealed vessel under pressure and at a temperature from 120° to 180° C.

The invention also relates to the compounds of the formula (3) indicated above and to the process for their preparation in accordance with stage (a) of the process described above, the meanings and preferences mentioned above applying to R, X and the process parameters.

The invention also relates to piperidine-2,6-diones of the formula (4) indicated above and to the process for their preparation in accordance with stage (b) of the process described above, the meanings and preferences mentioned above applying to R, X and the process parameters.

The compounds of the formula (1) are for the most part novel. The invention also relates, therefore, to compounds of the formula

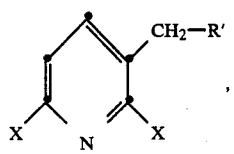

(1a)

in which X is halogen and R' is a heterocyclic aromatic radical or a radical of the formula

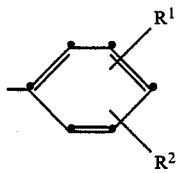

(5)

in which $R^1$ is $C_1$–$C_4$-alkyl, $C_1$–$C_4$-alkoxy, halogen, nitro, cyano, $C_1$–$C_4$-alkoxycarbonyl or trihalogenomethyl and $R^2$ independently is as defined for $R^1$ or, if $R^1$ is cyano, $C_1$–$C_4$-alkoxycarbonyl or trihalogenomethyl, is also hydrogen, subject to the provisos that, on the one hand, $R^1$ and $R^2$ are not both methyl and, on the other hand, $R^1 R^2$ is not nitro if the other substituent, $R^2$ or $R^1$, respectively, is chlorine.

Preferred compounds of the formula (1a) are those in which R' is a radical of the formula (5) indicated above, $R^1$ is cyano, $C_1$–$C_4$-alkoxycarbonyl or trihalogenomethyl and $R^2$ is hydrogen or nitro.

Compounds of the formula (1a) which are particularly preferred are those in which $R^1$ is a heterocyclic aromatic radical; in this case the meanings and preferences indicated above for R as a heterocyclic aromatic radical apply to R'.

The compounds of the formula (1) or (1a) can be prepared in accordance with stage (c) of the process described above from piperidine-2,6-dione compounds of the formula (4) indicated above; in this respect the meanings and preferences mentioned above apply in respect of the compounds of the formula (4) and the process parameters.

The compounds of the formulae (1) and (1a) are valuable intermediates, for example in the preparation of triarylmethane dyestuffs, which can be obtained by oxydation to give the diaryl ketone of the formula

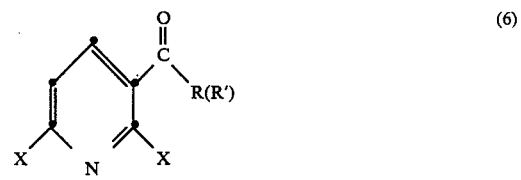

(6)

in which X, R and R' are each as defined above, and by reacting the ketone with a further aromatic compound.

If the aromatic radical R or R' in the compounds of the formula (6) contains an ester group or a functional group which can be converted into an ester group, for example cyano or trihalogenomethyl, in the orthoposition relative to the keto group, triarylmethanelactones which can be used, for example, as dye precursors are obtained.

The compounds of the formulae (1) and (1a) thus make it possible to gain access to an incalculable abundance of triarylmethane dyes and triarylmethanelactones, some of which are novel; a further area of operation relates to their use as intermediates for pharmaceuticals and plant protection agents.

The examples illustrate the invention without limiting it thereto.

PREPARATION OF THE DICYANOBUTANE COMPOUNDS IN ACCORDANCE WITH PROCESS STAGE (A)

EXAMPLE 1

500 ml of dimethyl methanephosphonate, 93 g of aniline, 152 g of concentrated hydrochloric acid, 159 g of 2-methyleneglutaronitrile and 0.75 g of copper-(I) chloride are together heated to 55°–60° C. The heating bath is removed and 123.2 g of isopentyl nitrite are added dropwise, with stirring (duratio approx. 1.5 hours, depending on the evolution of nitrogen and the rate at which heat is evolved in the reaction). The reaction mixture is stirred for a further 1.5 hours and is then poured into 2 litres of water; on standing, a solid product separates out from the oily suspension, and this is filtered off with suction, washed with water and recrystallized from methanol.

163 g (85%) of the compound of the formula

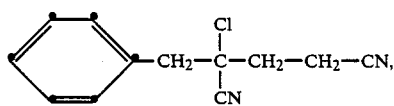

melting point 70°–71° C., are obtained.

EXAMPLE 2

10.7 g of 4-methylaniline, 50 ml of dimethyl methanephosphonate, 15.2 g of concentrated hydrochloric acid and 0.1 g of copper-(I) chloride are heated to 55° to 60° C., and 12.3 g of isopentyl nitrite are added dropwise, with stirring, in the course of 20 minutes.

The reaction mixture is stirred for a further 30 minutes and is poured into 150 ml of water. The product is then extracted with ether, and, after drying, the solvent is removed by evaporation in vacuo. The resulting oil is crystallized from methanol, and the solid is washed with cold methanol. Yield: 15.6 g (86%) of the compound of the formula

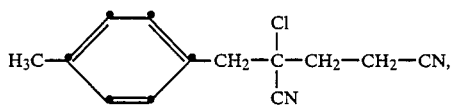

melting point 68°-69° C.

EXAMPLE 3

The procedure described in Example 1 or 2, is repeated, except that an equivalent amount of methyl nitrite is used instead of isopentyl nitrite, thus affording the compounds of Examples 1 or 2 in approximately the same quality.

EXAMPLE 4

The procedure described in Example 1 or 2 is repeated, except that the same amount by weight of ethylene glycol dimethyl ether, dimethylformamide or sulfolane is used instead of dimethyl methanephosphonate, thus affording in each case the compounds of Examples 1 or 2 in approximately the same quality.

EXAMPLES 5–22

The procedure of Examples 1 and 2 is repeated, except that the aromatic amines mentioned in the following table are used instead of aniline or 4-methylaniline, thus affording analogous compounds having the melting points mentioned in the table.

PREPARATION OF THE PIPERIDINE-2,6-DIONE COMPOUNDS IN ACCORDANCE WITH PROCESS STAGE (B)

EXAMPLE 23

6.55 g of 1-phenyl-2-chloro-2,4-dicyanobutane according to Example 1, 16.5 ml of acetic acid and 3.7 g of 78% $H_2SO_4$ are together heated under reflux for 2 hours. The product is filtered off, and is washed with water to give 6.25 g of the compound of the formula

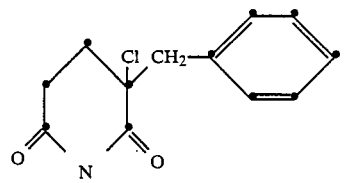

melting point, after recrystallization from acetonitrile, 157°–158° C.

EXAMPLE 24

11.0 g of 1-(pyridin-3-yl)-2-chloro-2,4-dicyanobutane according to Example 18, 55 ml of acetic acid and 12.5 g of 78% $H_2SO_4$ are together heated under reflux for 15 hours. The reaction mixture is added to a mixture of ice and 30% sodium hydroxide solution, and the product is then filtered off, washed with water and recrystallized from acetonitrile. This gives 8,9 g (75%) of the compound of the formula

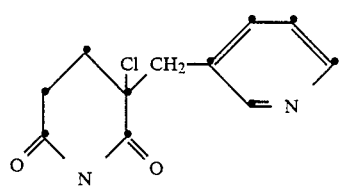

melting point 147°–148° C.

| Example | Aromatic amine R—NH$_2$ | Melting Point of the compound R—CH$_2$—C(Cl)(CN)—CH$_2$—CH$_2$—CN [° C.] | Yield [%] |
|---|---|---|---|
| 5 | 4-methoxyaniline | 55–55.5 | 82 |
| 6 | 4-chloroaniline | 68–70 | 51 |
| 7 | fluoroaniline | oil | 58 |
| 8 | 3-trifluoromethylaniline | 50.5–51 | 80 |
| 9 | 4-nitroaniline | 99–100 | 84 |
| 10 | 2-methoxycarbonylaniline | oil | 60 |
| 11 | 4-methoxycarbonylaniline | 72–73 | 76 |
| 12 | 2,5-dichloroaniline | 68–69 | 65 |
| 13 | 3,4-dichloroaniline | 105.5–106.5 | 73 |
| 14 | 2-methyl-4-nitroaniline | 84–85 | 64 |
| 15 | 2-trifluoromethyl-5-nitroaniline | oil | 38 |
| 16 | 3-nitro-4-chloroaniline | 99–100 | 62 |
| 17 | 4-cyanoaniline | 143–144 | 82 |
| 18 | 3-aminopyridine | 89–91 | 43 |
| 19 | 2-chloro-3-aminopyridine | 109–110 | 68 |
| 20 | 2,6-dichloro-3-aminopyridine | 77–78 | 66 |
| 21 | 2,5,6-trichloro-3-aminopyridine | 112–113 | 35 |
| 22 | 2-methoxycarbonyl-3-aminothiophene | 53.5–55 | 60 |

EXAMPLES 25–43

The 1-phenyldicyanobutane derivatives listed in the table are heated for 2 to 6 hours, and the 1-pyridyldicyanobutane derivatives are heated for 15 to 17 hours, analogously to Examples 23 or 24, respectively, under reflux in a mixture of acetic acid and sulfuric acid, thus affording analogous piperidine-2,6-dione compounds having the melting points indicated in the table.

| Example | Dicyanobutane compound R—CH₂—C(Cl)(CN)—CH₂—CH₂—CN, R = | Piperidine-2,6-dione compound Melting point [°C.] | Yield [%] |
|---|---|---|---|
| 25 | 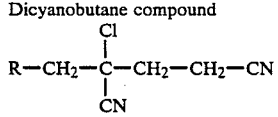 H₃C— | 197–198 | 95 |
| 26 | 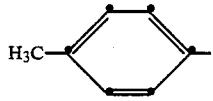 H₃CO— | 140.5–141 | 90 |
| 27 | 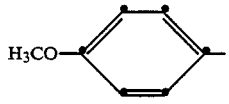 Cl— | 161–162 | 96 |
| 28 |  F— | 171–173 | 96 |
| 29 | 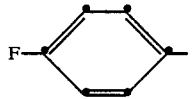 F₃C— | 127.5–129 | 22 |
| 30 | 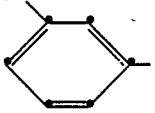 O₂N— | 191–192 | 96 |
| 31 | 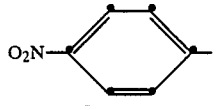 —COOCH₃ | 113–114 | 51 |
| 32 | 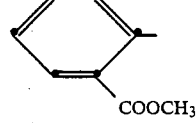 H₃COOC— | 172–174 | 95 |
| 33 | 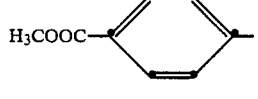 Cl, Cl | 199–200.5 | 96 |

-continued
| | Dicyanobutane compound R—CH₂—C(Cl)(CN)—CH₂—CH₂—CN | Piperidine-2,6-dione compound | |
|---|---|---|---|
| Example | R = | Melting point [°C.] | Yield [%] |
| 34 | 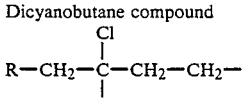 | 151–152 | 99 |
| 35 | 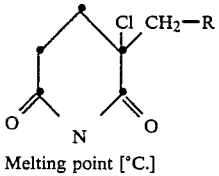 | 228–229 | 97 |
| 36 | 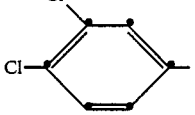 | 185–186 | 91 |
| 37 | 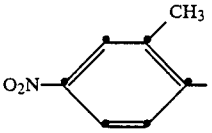 | 173–173.5 | 99 |
| 38 | 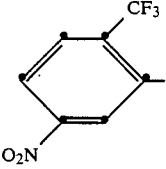 | 163–165 | 82 |
| 39 | 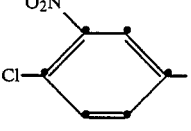 | 147–148 | 75 |
| 40 |  | 189–190 | 79 |
| 41 | 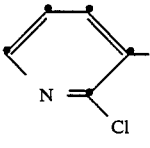 | 147–148 | 75 |
| 42 | 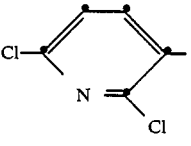 | 217–218 | 70 |

-continued

| | Dicyanobutane compound<br>R—CH₂—C(Cl)(CN)—CH₂—CH₂—CN | Piperidine-2, 6-dione compound<br>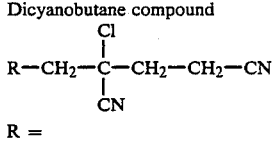 | | |
|---|---|---|---|---|
| Example | R = | Melting point [°C.] | | Yield [%] |
| 43 | 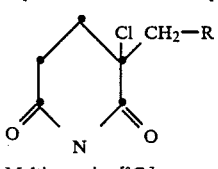 | 146–148 | | 90 |

PREPARATION OF THE 3-ARYLMETHYLPYRIDINE COMPOUNDS IN ACCORDANCE WITH PROCESS STAGE (C)

EXAMPLE 44

4.75 g of 3-chloro-3-benzylpiperidine-2,6-dione according to Example 23, 7.6 ml of phosphorus oxychloride and 1.0 g of hexamethylphosphoric acid triamide (HMPT) are together heated under reflux for 7 hours. After cooling, the reaction mixture is poured into cold water and stirred for a further 20 minutes. The aqueous suspension is extracted with ether, and the combined ether extracts are dried. Removing the solvent by evaporation in vacuo gives an oil, which is distilled at 118°–120° C./0.02 mm Hg. 2.4 g (50%) of the compound of the formula

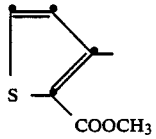

are obtained.

EXAMPLE 45

4.08 g of 3-chloro-3-(4-chlorobenzyl)-piperidine-2,6-dione according to Example 27 and 22 ml of phosphorus oxychloride are heated in an autoclave to a temperature of 170° C. and are kept at this temperature for 3 hours. The reaction mixture is then added slowly to 120 ml of water and is stirred for 20 minutes. The product is taken up in ether, the ethereal solution is washed with water, and the solvent is then removed by evaporation in vacuo. This gives 3.1 g (76%) of the compound of the formula

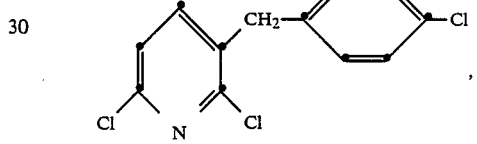

melting point 82°–84° C.

EXAMPLE 46

56.5 g of 3-chloro-3-(4-nitrophenyl)-piperidine-2,6-dione according to Example 30, 300 ml of phosphorus oxychloride and 20.5 g of HMPT are heated in an autoclave for 3 hours at 150°–160° C. The reaction mixture is added slowly to 2,400 ml of water, and the whole mixture is stirred for 1 hour. The crude product is filtered off, washed with water and transferred to a Soxhlet, where it is extracted with ether. Removing the solvent by evaporation in vacuo gives 42.8 g (91%) of the compound of the formula

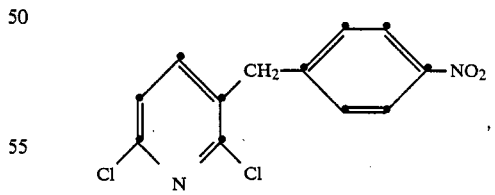

melting point 131°–132° C.

EXAMPLES 47–63

The procedure of Example 44, 45 or 46 is repeated, except that the piperidine-2,6-dione compounds indicated in the table are used, thus affording analogous 3-arylmethylpyridine compounds:

| Example | Piperdine-2,6-dione compound R = | 3-arylmethylpyridine Melting point [°C.] | Yield [%] |
|---|---|---|---|
| 47 | H3C—⌬— | Oil | 73 |
| 48 | H3CO—⌬— | Oil | 49 |
| 49 | F—⌬— | 73–74 | 55 |
| 50 | F3C-⌬- (ortho) | Oil | 72 |
| 51 | ⌬—COOCH3 (ortho) | 69–70 | 56 |
| 52 | H3COOC—⌬— | Oil | 41 |
| 53 | Cl-⌬- with Cl | 57–58 | 72 |
| 54 | Cl, Cl-⌬- | 94.5–96 | 93 |
| 55 | O2N—⌬—CH3 | 118–119 | 67 |
| 56 | CF3, O2N—⌬— | 79–79.5 | 46 |

-continued

| | Piperdine-2,6-dione compound | 3-arylmethylpyridine | |
|---|---|---|---|
| Example | R = | Melting point [°C.] | Yield [%] |
| 57 | O₂N—⟨Cl-phenyl⟩— | 91–92 | 88 |
| 58 | NC—⟨phenyl⟩— | 87–88 | 41 |
| 59 | ⟨pyridyl⟩ | 55–56 | 52 |
| 60 | ⟨Cl-pyridyl⟩ | 108–109 | 83 |
| 61 | Cl—⟨pyridyl⟩—Cl | 142–143 | 82 |
| 62 | Cl,Cl—⟨pyridyl⟩—Cl | 107–108.5 | 40 |
| 63 | ⟨thienyl⟩—COOCH₃ | 103–104 | 23 |

What is claimed is:

1. A process for the preparation of a compound of the formula

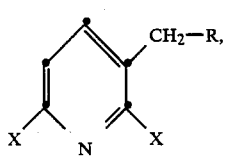

(1)

in which X is halogen and R is a phenyl, naphthyl, pyridyl or thienyl radical which is unsubstituted or substituted by $C_1$–$C_4$-alkyl, $C_1$–$C_4$alkoxy, halogen, nitro, cyano, trifluoromethyl or $C_1$–$C_4$-alkoxycarbonyl, with comprises the following process stages:

(a) diazotizing a compound of the formula $$R-NH_2 \qquad (2)$$

in the presence of a polar organic solvent, hydrochloric or hydrobromic acid and an ester of nitrous acid having 1 to 5 C-atoms, and reacting the diazotized compound with 2-methyleneglutaronitrile in the presence of a catalyst selected from the group consisting of metals of Group VIII or Ib, a salt of said metals and a mixture of a corresponding metal salt and metal powder, (b) cyclizing the compound of the formula

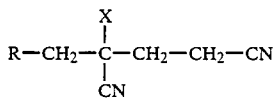

obtained in accordance with (a) in an acid medium to give the piperidine-2,6-dione compound of the formula

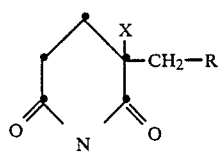

and (c) aromatizing the piperidine-2,6-dione compound of the formula (4) at a temperature of 50° to 250° C. in phosphorus oxybromide or phosphorus oxychloride without a catalyst or in the presence of hexamethylphosphoric acid triamide as catalyst, R and X each being as defined in formula (1).

2. A process according to claim 1, wherein X represents chlorine.

3. A process according to claim 1, wherein R is a phenyl radical which is unsubstituted or substituted by methyl, ethyl, methoxy, ethoxy, chlorine, fluorine, nitro, cyano, methoxycarbonyl, ethoxycarbonyl and/or trifluoromethyl.

4. A process according to claim 1, wherein R is a pyridin-3-yl or thien-3-yl radical which is unsubstituted or substituted by methyl, chlorine, methoxycarbonyl or ethoxycarbonyl.

5. A process according to claim 1, wherein the polar organic solvent used in process stage (a) is a dimethyl alkanephosphonate, $C_1$-$C_4$-alkanol, $C_1$-$C_4$ ketone, $C_4$-$C_{10}$ glycol ether, formamide which is unsubstituted or monosubstituted or disubstituted by $C_1$-$C_4$alkyl, or a cyclic sulfone.

6. A process according to claim 5, wherein a dimethyl $C_1$-$C_2$alkanephosphonate, methanol, acetone, diethylene glycol dimethyl ether, diethylene glycol diethyl ether, N,N-dimethylformamide or sulfolane is used.

7. A process according to claim 6, wherein dimethyl methanephosphonate is used as the polar organic solvent.

8. A process according to claim 1, wherein the catalyst used is 0.1 to 5% by weight, relative to the compound of the formula (2), of copper-(I) chloride.

9. A process according to claim 1, wherein the diazotization and the reaction with 2-methyleneglutaronitrile are carried out simultaneously at a temperature from 35° to 75° C.

10. A process according to claim 1, wherein the cyclization according to process stage (b) is carried out in a mixture of sulfuric acid and acetic acid.

11. A process according to claim 1, wherein the aromatization according to process stage (c) is carried out in the presence of hexamethylphosphoric acid triamide as catalyst.

12. A process according to claim 1, wherein the aromatization according to (c) is carried out in a closed vessel under pressure.

13. A process according to claim 1, wherein the aromatization of the compounds of the formula (4) is carried out in the presence of phosphorus oxychloride or oxybromide and hexamethylphosphoric acid triamide at a temperature from 120° to 180° C., under pressure.

14. A process for the preparation of compounds of the formula (1) according to claim 1, wherein the process stages are as follows:

(a) Diazotization of a compound of the formula (2) according to claim 1 in the presence of an ester of nitrous acid having 1 to 5 C atoms, hydrochloric acid and dimethyl methanephosphonate, and simultaneous reaction of the diazotized compound with 1 to 5 mol of 2-methyleneglutaronitrile per mol of amine of the formula (2) in the presence of 0.1 to 5% by weight of copper powder, copper-(I) chloride or copper-(II) chloride, relative to the amine of the formula (2), at a temperature from 35° to 75° C. to give the compound of the formula (3) according to claim 1, (b) Cyclization of the compound of the formula (3) according to claim 1 in a mixture of sulfuric acid and acetic acid at a temperature from 40° to 200° C. to give the piperidine-2,6-dione compound of the formula (4) according to claim 1, and (c) Aromatization of the compound of the formula (4) according to claim 1 in the presence of excess phosphorus oxychloride or oxybromide and 5-15% by weight of hexamethylphosphoric acid triamide, relative to the phosphorus oxyhalide, in a closed vessel under pressure and at a temperature from 120° to 180° C.

* * * * *